United States Patent [19]

Redha

[11] Patent Number: 5,282,813
[45] Date of Patent: Feb. 1, 1994

[54] SURGICAL APPARATUS FOR REMOVAL OF DEPOSITS FROM VESSELS

[76] Inventor: Falah Redha, Linden Strasse 17, 8302 Kloten, Switzerland

[21] Appl. No.: 867,829

[22] Filed: Apr. 10, 1992

Related U.S. Application Data

[63] Continuation-in-part of Ser. No. 499,313, Jul. 9, 1990, Pat. No. 5,152,773.

[51] Int. Cl.$^5$ .............................................. A61B 17/32
[52] U.S. Cl. .................................. 606/159; 606/170; 604/22
[58] Field of Search ............................ 606/159–161, 606/167–171; 604/22, 19; 128/751, 753, 754, 755

[56] References Cited

U.S. PATENT DOCUMENTS

| | | |
|---|---|---|
| 2,868,206 | 1/1959 | Stoesser . |
| 3,230,949 | 1/1966 | Rodriguez-Olleros . |
| 3,508,553 | 4/1970 | Kanbar et al. . |
| 3,764,427 | 10/1973 | Reimels . |
| 3,837,345 | 9/1974 | Matar .................. 606/159 |
| 4,273,128 | 6/1981 | Lary . |
| 4,493,321 | 1/1985 | Leather . |
| 4,685,458 | 8/1987 | Leckrone . |
| 4,747,821 | 5/1988 | Kensey et al. . |
| 4,765,332 | 8/1988 | Fischell et al. . |
| 4,794,928 | 1/1989 | Kletschka . |
| 4,842,579 | 6/1989 | Shiber . |
| 4,886,061 | 12/1989 | Fischell et al. . |
| 4,952,215 | 8/1990 | Ouriel et al. . |
| 4,957,482 | 9/1990 | Shiber . |
| 5,026,383 | 6/1991 | Nobles . |
| 5,047,041 | 9/1991 | Samuels . |
| 5,049,154 | 9/1991 | Quadri . |
| 5,053,044 | 10/1991 | Mueller et al. .......... 606/159 |
| 5,061,240 | 10/1991 | Cherian . |
| 5,069,679 | 12/1991 | Taheri ................... 606/159 |
| 5,071,424 | 12/1991 | Reger ..................... 606/159 |
| 5,074,871 | 12/1991 | Groshong . |
| 5,100,426 | 3/1992 | Nixon ..................... 606/170 |
| 5,133,725 | 7/1992 | Quadri .................... 606/159 |
| 5,152,772 | 10/1992 | Sewell .................... 606/159 |
| 5,152,773 | 10/1992 | Redha ..................... 606/159 |
| 5,154,724 | 10/1992 | Andrews .................. 606/159 |
| 5,178,625 | 1/1993 | Groshong ................. 606/159 |
| 5,192,291 | 3/1993 | Pannek ................... 606/159 |
| 5,211,651 | 5/1993 | Reger et al. ............. 606/159 |

FOREIGN PATENT DOCUMENTS

| | | |
|---|---|---|
| 0117519 | 2/1984 | European Pat. Off. . |
| 1909080 | 11/1964 | Fed. Rep. of Germany . |
| 3320984 | 12/1984 | Fed. Rep. of Germany . |
| 3800777 | 7/1988 | Fed. Rep. of Germany . |
| 1585065 | 1/1970 | France . |
| 89/09029 | 10/1989 | PCT Int'l Appl. . |
| 2044103 | 10/1980 | United Kingdom . |

*Primary Examiner*—C. Fred Rosenbaum
*Assistant Examiner*—Mark O. Polutta
*Attorney, Agent, or Firm*—Speckman, Pauley & Fejer

[57] ABSTRACT

A medical apparatus for removing deposits from arterial and venous walls comprising a partially hollow body, essentially circular in cross-section, having an insertion end and a withdrawal end. At least two shell-shaped parts extend from the insertion end towards the withdrawal end pivotally connected to the body proximate the insertion end and forming a cutting edge distal from the insertion end. The shell-shaped parts have a convex surface towards the cutting edge facing away from the body such that the cutting edge generally faces toward the central axis of the body of the apparatus. At least two leaf arms pivotally connected at one end to each other, the other end of each leaf arm being pivotally connected to one of the shell-shaped parts, are disposed inside the partially hollow body and are connected to means for expanding the shell-shaped parts. Means for withdrawing the body from a vessel are connected to the withdrawal end of the body.

19 Claims, 4 Drawing Sheets

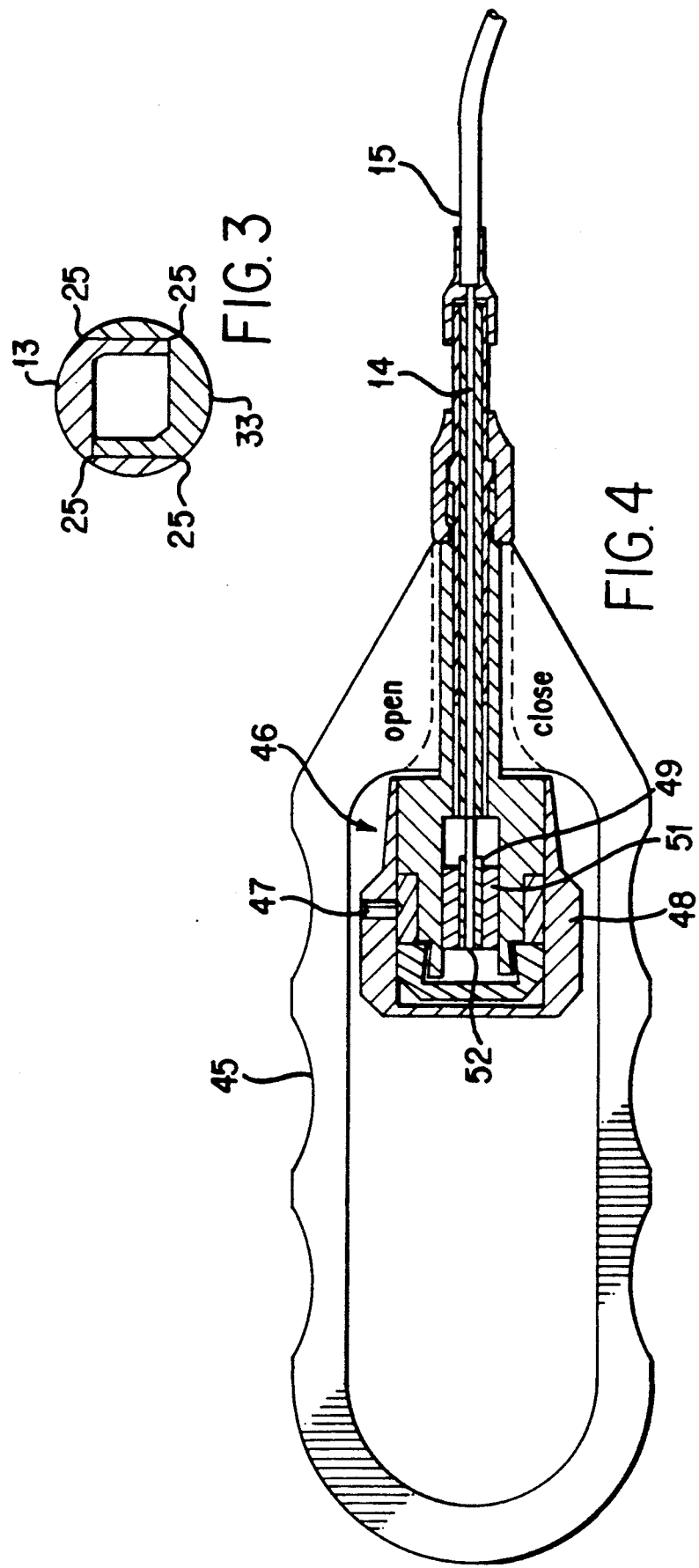

SURGICAL APPARATUS FOR REMOVAL OF DEPOSITS FROM VESSELS

CROSS REFERENCE TO RELATED APPLICATION

This application is a continuation-in-part of co-pending U.S. patent application Ser. No. 07/499,313, Filing Date Jul. 9, 1990 now U.S. Pat. No. 5,152,773.

BACKGROUND OF THE INVENTION

1. Field of the Invention

This invention relates to a medical apparatus for the removal of deposits, such as plaque, from the walls of arteries and/or veins, which is vessel-insertable, practical, withdrawable and directable, and which eliminates such deposits by slicing off portions with cutting edges.

2. Description of the Prior Art

Arteriosclerosis, a chronic, progressive, degenerative disease, particularly when located on the inner surface of artery walls, is an illness occurring frequently in the civilized world, most commonly during the second half of normal life spans. For example, about 90% of such cases are the cause of arterial blockage diseases, one of the most frequent causes of death. As a result of penetration of thrombocytes in the cell interspaces, followed by lipoid-containing deposits, the inner-most portion of walls of the vessels develops what is known as atheromas changes, which leads to the death of cells and, finally, expands the connecting tissue at this artery wall site (sclerosis). As a result of these changes, the artery wall loses its normal elasticity. Focal deposits, especially Cholesterin crystals that also penetrate to the middle of the vessel wall, lead to inflammatory reactions and more cell deaths. This results in calcium deposits, which cause growths in the vessel lumen and later produce thrombosis.

In some cases, arteriosclerosis can be treated with medicines, dilating the vessel to increase the flow of blood. In some cases, physio-therapeutic methods have been shown to improve circulation. In still other instances, surgical procedures have been developed to treat arteriosclerosis. The surgical treatment of arteriosclerosis changes when particular organs or parts of the body are involved. Vascular surgery can be successfully applied, particularly in the following cases:
a) Arteriosclerosis alteration to the carotid artery which supplies blood to the brain;
b) Arteriosclerosis alteration to the coronary arteries, that is, coronary bypass and implanting;
c) Serious arteriosclerosis which affects the supply of blood to the extremities;
d) Arteriosclerosis to the kidney arteries; and
e) The removal of aneurisms.

With arteriosclerosis change, the following surgical techniques are generally applied:
a) Bypass surgery during which the plugged artery is replaced by a section of the patient's vein or artery or synthetic material in the form of a vessel, to bridge the flow of blood into certain areas;
b) Endarterectomy;
c) Implanting of a patch after endarterectomy;
d) Implanting of a vessel prosthesis, either as a replacement or bypass for the arteriosclerosis artery;
e) Sympathectomy;
f) Removing arteriosclerosis changes using a balloon catheter.

It is known that arteriosclerosis changes are located mainly on internal walls of arteries, while the external walls remain relatively normal. When intersclerotic material is removed or sliced from the internal wall, the surface is left smooth. U.S. Pat. No. 4,765,332 teaches an atherectomy apparatus for surgical excision of atheromas, such as plaque deposits in an artery. The apparatus, after insertion into the desired vessel, operates by first penetrating the plaque in a forward direction with a conically-pointed metal tip and then pulling the tip back in a retrograde direction, which tip includes a cylindrical cutting edge, to shave off a cylindrical layer of the plaque. To enlarge the lumen of the plaque, sequentially larger diameter tips are progressively used. In addition to the necessity of changing tips to progressively enlarge the lumen of the plaque, an obvious disadvantage, this device has the further disadvantage that the sharp edges of the cutting portion of the tip are directed from the inside to the outside of the vessel, which could lead to the injury of healthy vessels. Similar devices are also taught by German reference 1,909,080, which discloses a probe having a protecting cap with a cutting edge connected to a tube which runs through a body which is movable toward the protecting cap such that material which is sliced from the arterial wall is retained within the protecting cap; British patent application GB 2,044,103 which teaches a cutting device for removing material from stenoses within blood vessels having a head mounted in tandem with a body, both the head and body having cutting edges such that, when inserted into a blood vessel, the head and body are positioned on opposite sides of the stenoses to be removed, the head being drawn toward the body causing the cutting edges on the head and the body to cut through the stenoses; U.S. Pat. No. 5,074,871, which teaches a catheter atherotome, for performing partial atherectomy in an artery having an expansible cutter head; U.S. Pat. No. 4,957,482 and related U.S. Pat. No. 4,842,579, which teach a flexible rotary catheter for cutting, ingesting and removing an obstruction from an artery; and U.S. Pat. No. 4,747,821, which discloses a flexible, small diameter catheter having a working head with a non-sharp impacting surface which is rotated at a high rate of speed by an associated drive means within the catheter.

Other devices for effecting openings in arteries clogged with plaque are taught by European Patent Application 0,117,519 which discloses a catheter having electrical terminals and a probe with a screw-type element disposed therein for expanding the circumference of the probe for pushing through the clogged artery; French reference 1,585,065, which discloses a surgical instrument for breaking through plaque and arteries; German reference DE 3,800,777 A1, which discloses a thermal, sound apparatus with laser means for angioplasty drawing pins; and German reference DE 3,320,984 A1, which discloses a catheter having an end portion, the circumference of which is expandable, for pushing through a blockage.

See also U.S. Pat. No. 5,047,041, which teaches a surgical device for cutting and removing venous valves, having a valve cutter with a fixed, non-expandable, circular cutting head affixed to a cable or wire, the cutting edge of which slices through the material to be removed as the device is pulled through a vein; U.S. Pat. No. 4,952,215, which teaches a valve valvulotome for preparing veins in situ for arterial bypass; U.S. Pat. No. 5,026,383, which teaches an apparatus for in situ cutting through one-way valves in a vein having a cutting catheter and a pulling catheter, the pulling catheter being advanced through the vein in a normal direction of blood flow and then connected to a cutting catheter and pulled back reversely through the one-way valves, the valve cusps of which are severed by cutting blades on the cutting catheter; U.S. Pat. No. 5,061,240, which teaches a balloon-tip catheter for tearing away one-way valves in a vein having an arrowhead shape when inflated, with an annular groove formed in the arrowhead base adjacent to and extending around the catheter tube; U.S. Pat. No. 5,049,154, which teaches an adjustable intraluminal valvulotome; U.S. Pat. No. 4,794,928, which teaches an angioplasty device having an operative member for removing and/or crushing an obstruction in a vessel such as a balloon, cutting rotors, fiber meshes and lasers; U.S. Pat. No. 4,685,458, which teaches a catheter having an element such as a fiber optic emitting laser energy, a heated element or a knife for intersecting and releasing undesired material in a blood vessel; U.S. Pat. No. 4,493,321, which teaches a venous valve cutter having a blade drawn by a rod attached centrally so that a portion of the blade extends on either side of the rod; U.S. Pat. No. 4,273,128, which teaches a coronary cutting and dilating instrument having a flexible probe at a distal end for guidance through a coronary artery followed, in succession, by one or more radially-extending knife blades for making a coronary incision and an inflatable balloon for dilating the stenotic artery zone immediately after the incision; U.S. Pat. No. 3,764,427, which teaches a vein-stripping instrument having a cable formed from a mono-filament of axially-oriented synthetic thermoplastic material, with a tubular plastic cap ultrasonically welded to each end; U.S. Pat. No. 3,508,553, which teaches a surgical vein-stripping instrument, having a cable with rounded end portions to which are attached bullet-shaped tips; U.S. Pat. No. 3,230,949, which teaches a gastroesophageal catheter having a flexible tube with a head attached to one end, the head comprising a plurality of cutting apertures communicating with the interior of the tube; U.S. Pat. No. 2,868,206, which teaches a vein stripper having an elongated slender wire and a bucket member slidable thereon; and International Patent Application PCT/US89/00634, which teaches a valvulectome, having an elongated probe with a tip and an actuating rod which moves a pair of blade members between retracted and expanded positions.

SUMMARY OF THE INVENTION

It is an object of this invention to provide a medical apparatus for removing deposits, in particular asymmetric deposits, from vessel walls without damaging the vessel walls.

It is another object of this invention to provide a medical apparatus for removing deposits from vessel walls which prevents material removed from the vessel walls from entering the blood stream.

It is yet another object of this invention t provide a medical apparatus for removing deposits from vessels which is remotely adjustable to permit incremental removal of such deposits.

These and other objects are achieved by a medical apparatus, in accordance with one embodiment of this invention, comprising a partially hollow body, having an insertion end and a withdrawal end, which is essentially circular in cross section. At least two shell-shaped parts are pivotally connected to the body towards the insertion end thereof, each shell-shaped part extending from the insertion end to the withdrawal end of the body and having a cutting edge proximate the withdrawal end. Each shell-shaped part is provided with a surface toward said cutting edge and facing away from said body which is convex in a direction facing away from the body such that a tangential line intersecting the convex surface and a central axis of the body forms an angle there between, the angle having a tangent which increases as the tangential line intersects the convex surface closer to the cutting edge. The angle thus formed is preferably between about 10° and about 90° when the tangential line intersects the cutting edge.

In accordance with one embodiment of this invention, at least one longitudinal edge of each shell-shaped part has an auxiliary cutting edge.

In accordance with one embodiment of this invention, the cutting edges and/or the auxiliary cutting edges have a corrugated pattern.

Means for withdrawing the partially hollow body from a vessel are connected to the body, said means for withdrawing extending from the withdrawal end of the body. At least two leaf arms pivotally connected at one end to control means for expanding and/or contracting the shell-shaped parts are disposed within the body, the other end of each leaf arm being pivotally connected to one of the shell-shaped parts. The control means for expanding and/or contracting the shell-shaped parts are coextensive with said means for withdrawing the partially hollow body and are operatively connected to the leaf arms such that the ends of the leaf arms connected to the shell-shaped parts are forced apart, resulting in expansion of the shell-shaped parts, when the control means for expanding and/or contracting the shell-shaped parts is in an expanding operative mode.

The shell-shaped parts are constructed of metal, ceramic, or plastic materials, or mixtures thereof. In accordance with one embodiment of this invention, the shell-shaped parts are constructed of a memory metal or self-expanding metal, such as Flexinol TM shape memory alloy actuator wires made of nickel-titanium, which enables the shell-shaped parts to expand automatically under certain circumstances, most notably an increase in temperature. In this case, the control means for expanding and/or contracting the shell-shaped parts are required only for contracting the shell-shaped parts.

Connected to the pivotally-connected leaf arm ends, in accordance with one embodiment of this invention, is a cable, which is operable to force the distal ends of the leaf arms apart, thereby expanding the shell-shaped parts, or pull the distal ends together, thereby contracting the shell-shaped parts. Surrounding the length of the cable is a housing, one end of which is secured to the withdrawal end of the body. Connected to the distal end of the cable are means for extending the cable into the body, thereby operatively forcing the distal ends of the leaf arms apart.

In accordance with one embodiment of this invention, the ends of the shell-shaped parts having the cutting edges extend beyond the connection of the housing to the body, the shell-shaped parts forming a cavity around the body. The housing is connected to the body by a housing endpiece which is provided with a circumferential barb extending toward the shell-shaped parts and, having a circumferential cutting edge substantially in contact with the inside surface of the shell-shaped parts when the shell-shaped parts are in a non-expanded, or contracted, position.

In accordance with yet another embodiment of this invention, the apparatus is provided with means for directing the body along a guide wire for controlling movement of the body within the vessel.

BRIEF DESCRIPTION OF THE DRAWINGS

Further features of this invention will be apparent from the following more detailed description taken in conjunction with the drawings, wherein:

FIG. 3 is a cross-sectional end view of the shell-shaped parts of the medical apparatus in accordance with one embodiment of this invention;

FIG. 4 is a cross-sectional view of a handle and mechanism for controlling movement of a cable pivotally connected to the leaf arms of the medical apparatus in accordance with one embodiment of this invention;

DESCRIPTION OF PREFERRED EMBODIMENTS

Figure 5:
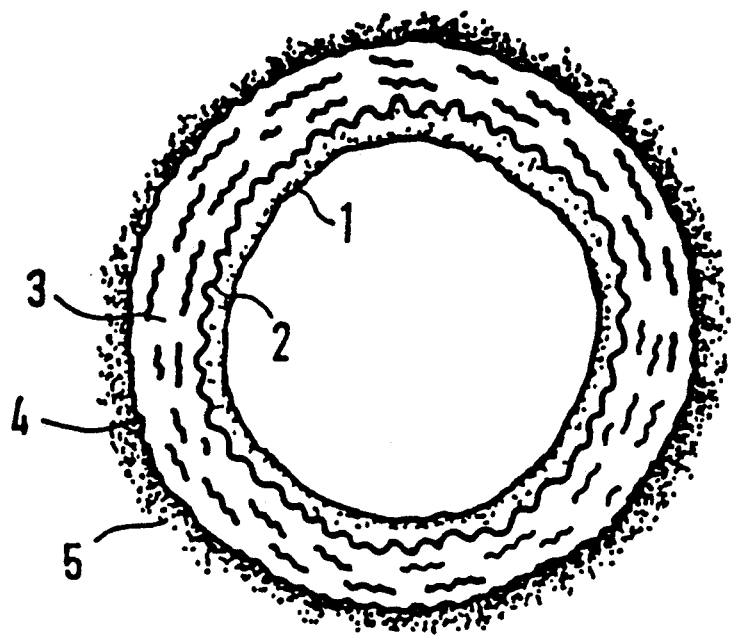
FIG. 5 is a cross-sectional view of a healthy artery wall.
Figure 6:
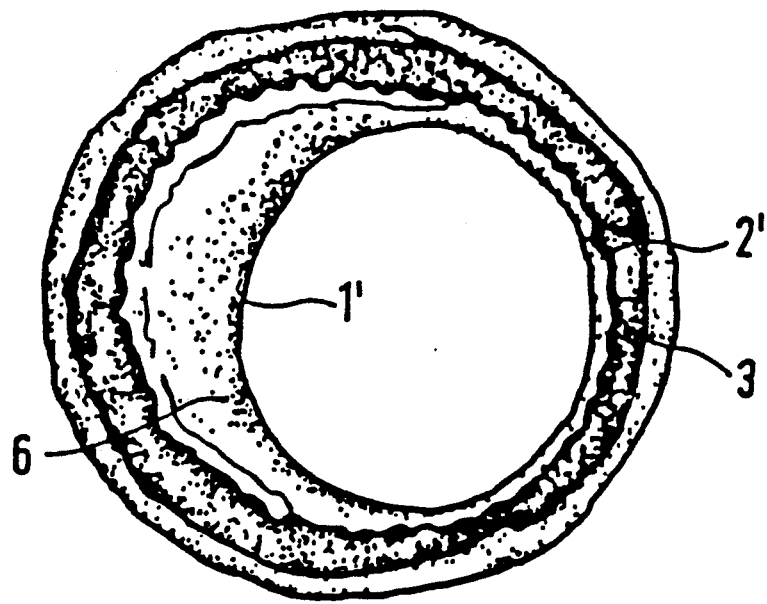
FIG. 6 is a cross-sectional view of an artery wall with arteriosclerosis.

FIG. 5 shows a cross section of a healthy artery wall, while FIG. 6 shows a cross section of an artery with arteriosclerosis. The healthy artery wall consists of Intima 1, Elastica Interna 2, Media 3, Elastica Externa 4, and Adventitia 5. In a artery wall having arteriosclerosis, as shown in FIG. 6, Intima 1' is thickened with connective tissue. So, too, is Elastica Interna 2' Between Elastica Interna 2' and Intima 1', there is a metrotic Intim pocket containing cholesterol 6.

Figure 1:
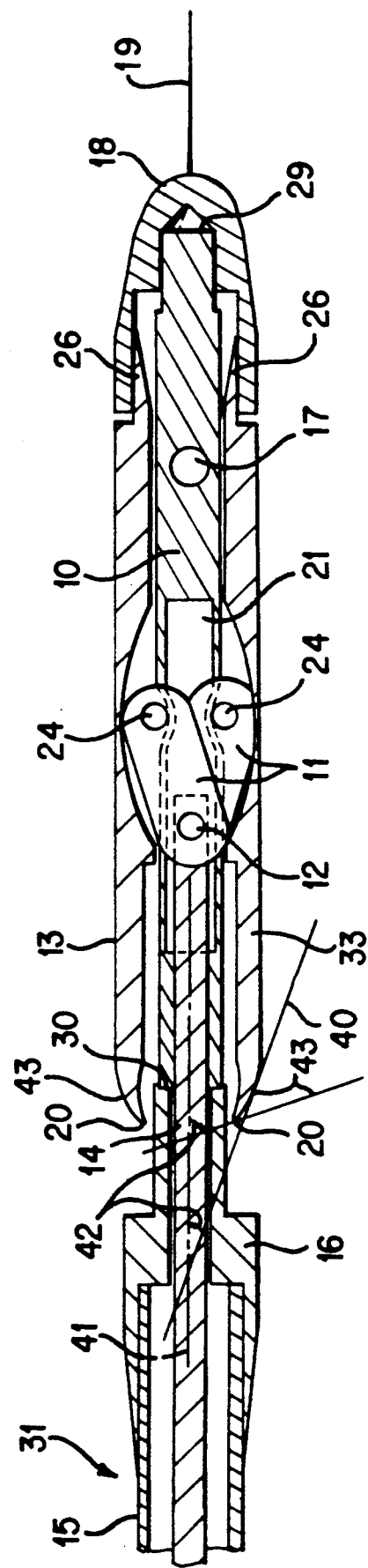
FIG. 1 is a cross-sectional side view of a portion of the medical apparatus in accordance with one embodiment of this invention.
Figure 2:
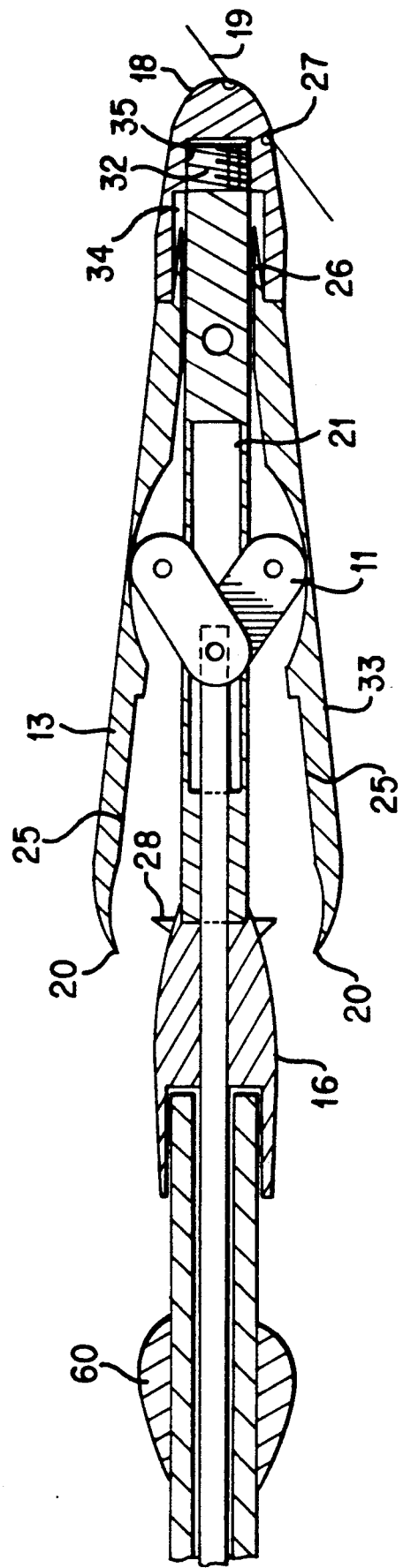
FIG. 2 is a cross-sectional side view of the portion of the medical apparatus shown in FIG. 1 in accordance with another embodiment of this invention.

The medical apparatus in accordance with this invention as shown in FIGS. 1 and 2 is specifically designed for insertion into arteries. The apparatus comprises partially hollow body 10 having insertion end 29 and withdrawal end 30. Connected to withdrawal end 30 of partially hollow body 10 is withdrawal cable 31 comprising control cable 14, cable housing 15 and cable housing endpiece 16. One end of control cable 14 is pivotally connected to arm pivot pin 12 to which one end of each of leaf arms 11 is also connected. Connected to insertion end 29 of body 10 is safety cap 18. In accordance with one embodiment of this invention, insertion end 29 of body 10 is provided with threads 32 for securing safety ca 18 having threaded blind bore 35 to insertion end 29 of body 10. In accordance with another embodiment of this invention, safety cap 18 is press-fitted onto insertion end 29 of body 10. It is apparent that other suitable means for securing safety cap 18 to insertion end 29 of body 10 are also possible.

Shell-shaped parts 13, 33 are pivotally connected to body 10 through shell pin 17 disposed proximate insertion end 29 of body 10. Shell-shaped parts 13, 33 extend from insertion end 29 of body 10 toward withdrawal end 30 of body 10 and form cutting edges 20. The ends of leaf arms 11 distal from the end of cable 14 are pivotally connected to shell-shaped parts 13, 33 through arm/shell pivot pins 24, one end of each leaf arm 11 being pivotally connected to one of shell-shaped parts 13, 33 between shell pin 17 and arm pivot pin 12. Leaf arms 11 are disposed within slot 21 defined by body 10, slot 21 being positioned between shell pin 17 and withdrawal end 30 of body 10.

To expand shell-shaped parts 13, 33, cable 14 is moved toward insertion end 29 of body 10, thereby forcing the ends of leaf arms 11 pivotally connected to arm/shell pivot pins 24 away from body 10. This, in turn, causes shell-shaped parts 13, 33 to expand.

To limit the amount of expansion of shell-shaped parts 13, 33, safety cap 18 is secured to insertion end 29 of body 10. A portion of safety cap 18 extends toward withdrawal end 30 of body 10 and forms annulus 34 around body 10. Shell-shaped parts 13, 33 are provided with extensions 26 which taper toward insertion end 29 of body 10 and are insertable into annulus 34 formed by safety cap 18. Accordingly, movement of shell-shaped parts 13, 33 is limited to the extent that the movement of extensions 26 within annulus 34 is limited. Thus, in the event of failure of the mechanism for expanding shell-shaped parts 13, 33, expansion of shell-shaped parts 13, 33 is limited by the movement of extensions 26 within annulus 34, thereby preventing shell-shaped parts 13, 33 from opening further than desired and possibly causing injury to arterial walls.

A critical feature of the apparatus of this invention is the curvature of cutting edges 20 of shell-shaped parts 13, 33 inward toward the central axis of body 10. Specifically, each of shell-shaped parts 13, 33 is provided with convex surface 43 proximate cutting edge 20, which surface faces away from body 10 such that a tangential line 40 which intersects convex surface 43 and central axis 41 of body 10 forms an angle 42 there between, angle 42 having a tangent which increases as tangential line 40 intersects convex surface 43 of shell-shaped parts 13, 33, closer to cutting edge 20. When tangential line 40 intersects cutting edge 20, angle 42 is preferably between about 10° and about 90°. In this manner, cutting edges 20 are never in a position to cut into the arterial wall and damage said wall.

In accordance with another embodiment of this invention, shell-shaped parts 13, 33 form auxiliary cutting edges 25 along a longitudinal edge. Thus, as body 10 is pulled by means for withdrawing body 10 from a vessel connected to body 10, plaque deposited on vessel walls positioned lateral to shell-shaped parts 13, 33 is also sliced, and thus removed.

FIG. 3 shows the manner in which shell-shaped parts 13, 33 interlock when in a non-expanded mode. Thus, auxiliary cutting edges 25 create a scissors-like action on plaque deposits disposed therebetween when shell-shaped parts 13, 33 go from an expanded to a non-expanded position. In addition, plaque deposits removed from the venous walls are trapped within the cavity formed by shell-shaped parts 13, 33 and partially hollow body 10, preventing such deposits from breaking away and entering the blood stream.

In accordance with yet another embodiment of this invention, cable housing end piece 16 which connects cable housing 15 to withdrawal end 30 of body 10 is provided with circumferential barb 28 which extends toward shell-shaped parts 13, 33. When shell-shaped parts 13, 33 are in a non-expanded mode, circumferential barb 28 forms a circumferential cutting edge which is substantially in contact with an inside surface of shell-shaped parts 13, 33, thereby enhancing the cutting capability of the apparatus.

In accordance with another embodiment of this invention, guide wire 19 is used to direct body 10 through the vessels into which it is inserted toward the deposit to be removed. In accordance with one embodiment of this invention, guide wire 19 is inserted through opening 27 in safety cap 18. In accordance with another embodiment of this invention, guide wire 19 is inserted through an opening in body 10. It is apparent the guide wire 19 may be accommodated in any suitable opening through partially hollow body 10 and/or safety cap 18. In accordance with yet another embodiment of this invention, guide wire 19 is affixed to safety cap 18.

Means for controlling the movement of cable 14 within partially hollow body 10 are shown in FIG. 4 in which handle 45 and mechanism 46 for controlling the movement of cable 14 are shown secured to the distal end of cable housing 15. Mechanism 46 comprises rotatable hollow knob 48 having insert 51 fixedly disposed therein, insert 51 having a longitudinally extending threaded bore 52. Cable 14 is provided with threaded cable endpiece 49 which is threaded into bore 52. When knob 48 is rotated from an open position to a closed position as indicated on handle 45, cable endpiece 49 is drawn into insert 51 resulting in movement of the end of cable 14 operatively connected to leaf arms 11 away from insertion end 29 of partially hollow body 10. The ends of leaf arms 11 pivotally connected to shell-shaped parts 13, 33 are drawn towards each other, putting shell-shaped parts 13, 33 in a non-expanded position. Rotating knob 48 from the closed position to the open position pushes cable 14, and thus the ends of leaf arms 11 operatively connected thereto towards insertion end 29 of body 10, causing the ends of leaf arms 11 operatively connected to shell-shaped parts 13, 33 to move away from each other, putting shell-shaped parts 13, 33 in an expanded position. To limit the movement of cable 14, in particular to prevent cable 14 from being overextended into body 10, knob 48 is provided with stop 47 which limits the rotation of knob 48.

In accordance with another embodiment of this invention, bulbous guide body 60 as shown in FIG. 2 is attached to the exterior of cable housing 15 between said cutting edges 20 and said handle 45 connected to the distal end of cable housing 15, preferably proximate the end of cable housing 15 to which body 10 is attached. Guide body 60 serves to guide body 10 of the apparatus of this invention into a catheter opening when body 10 is being withdrawn from a vessel.

While in the foregoing specification, this invention has been described in relation to certain preferred embodiments thereof, and many details have been set forth for purpose of illustration, it will apparent to those skilled in the art that the invention is susceptible to additional embodiments and that certain of the details described herein can be varied considerably without departing from the basic principles of the invention.

I claim:

1. A medical apparatus for removing deposits from arterial and venous walls and for removing venous valves comprising:

a body having an insertion end and a withdrawal end, said body essentially circular in cross-section and partially hollow;

at least two shell-shaped parts extending from said insertion end towards said withdrawal end pivotally connected to said body proximate said insertion end and having a cutting edge proximate said withdrawal end, said shell-shaped parts having a convex surface proximate said cutting edge, said convex surface facing away from said body such that a tangential line intersection said convex surface and a central axis of said body forms an angle therebetween, said angle having a tangent which increases as said tangential line intersects said convex surface closer to said cutting edge, said angle being between about 10° and about 90° when said tangential line intersects said cutting edge;

control means for at least one of expanding and contracting said shell-shaped parts;

at least two leaf arms pivotally connected at one end to said control means, the other end of each said leaf arm being pivotally connected to one of said shell-shaped parts; and means for withdrawing said body from a vessel.

2. A medical apparatus in accordance with claim 1, wherein each of said shell-shaped parts comprises an auxiliary cutting edge along a longitudinal edge of each of said shell-shaped parts.

3. A medical apparatus in accordance with claim 1, wherein said control means for at least one of expanding and contracting said shell-shaped parts comprises a cable pivotally connected to said leaf arms, said cable extending from said withdrawal end of said body.

4. A medical apparatus in accordance with claim 1, wherein said shell-shaped parts are constructed of a material selected from the group consisting of metal, ceramic, plastic and mixtures thereof.

5. A medical apparatus in accordance with claim 4, wherein said metal is one of a memory metal and a self-expanding metal.

6. A medical apparatus in accordance with claim 3, wherein said shell-shaped parts form a cavity around said withdrawal end of said body and a housing is disposed around said cable and connected to said withdrawal end of said body.

7. A medical apparatus in accordance with claim 1, wherein a safety cap is attached to said insertion end of said body.

8. A medical apparatus in accordance with claim 1, wherein a safety cap is attached to said insertion end of said body, said safety cap forming an annulus around a portion of said body, and each, said shell-shaped part having an extension proximate said insertion end of said body, each said extension tapering toward said safety cap and extending into said annulus, restricting movement of said shell-shaped parts.

9. A medical apparatus in accordance with claim 1, wherein said body is provided with an opening for receiving a guide wire.

10. A medical apparatus in accordance with claim 8, wherein a guide wire is affixed to said safety cap.

11. A medical apparatus in accordance with claim 8, wherein said safety cap is provided with an opening for receiving a guide wire.

12. A medical apparatus in accordance with claim 1, wherein said control means for at least one of expanding and contracting said shell-shaped parts further comprises means for extending said cable into said body connected to a distal end of said cable.

13. A medical apparatus in accordance with claim 6, wherein a housing cap connects said housing to said body, said housing cap having a circumferential barb extending toward said shell-shaped parts, said circumferential barb forming a circumferential cutting edge substantially in contact with an inside surface of said shell-shaped parts when said shell-shaped parts are in a non-expanded position.

14. A medical apparatus in accordance with claim 1, wherein said body is axially symmetric.

15. A medical apparatus in accordance with claim 1, wherein said cutting edge has a corrugated pattern.

16. A medical apparatus in accordance with claim 2, wherein said auxiliary cutting edge has a corrugated pattern.

17. A medical apparatus in accordance with claim 1, wherein said withdrawal end of said body is provided with a longitudinal opening through which a cable is extended.

18. A medical apparatus in accordance with claim 1, wherein said body is provided with a longitudinally extending slot and said leaf arms are disposed within said longitudinally extending slot.

19. A medical apparatus in accordance with claim 6, wherein a guiding body is attached to said housing between said cutting edges of said shell-shaped parts and means for moving said cable into said body connected to a distal end of said cable.

* * * * *